United States Patent [19]

Murányi et al.

[11] 4,022,067
[45] May 10, 1977

[54] RAPID-ACTION AUTOMATIC SAMPLING APPARATUS

[75] Inventors: István Murányi; György Harsányi, both of Budapest, Hungary

[73] Assignee: Labor Muszeripari Muvek of Esztergom, Rudas Laszlo, Hungary

[22] Filed: Feb. 26, 1976

[21] Appl. No.: 661,503

[30] Foreign Application Priority Data

Mar. 7, 1975 Hungary .............................. LA 859

[52] U.S. Cl. ............................................. 73/423 A
[51] Int. Cl.² ......................................... G01N 1/14
[58] Field of Search ................................ 73/423 A

[56] References Cited

UNITED STATES PATENTS 3,178,266  4/1965  Anthon ............................ 73/423 A Primary Examiner—S. Clement Swisher

[57] ABSTRACT

The invention concerns a rapid-action automatic sampling apparatus comprising an intermittently operable sampling probe which is immersible alternately into a sample-containing vessel and a washing vessel. The probe is arranged on an arm secured to a vertical lifting rod which is journalled both for axial displacement and for rotation about its own axis and which is connected with a crank mechanism, including a swivel arm, for lifting or lowering the rod. There is a further mechanism for rotating the rod between two angular positions: this mechanism is arranged on the rod and its mounting and on the swivel arm.

2 Claims, 1 Drawing Figure

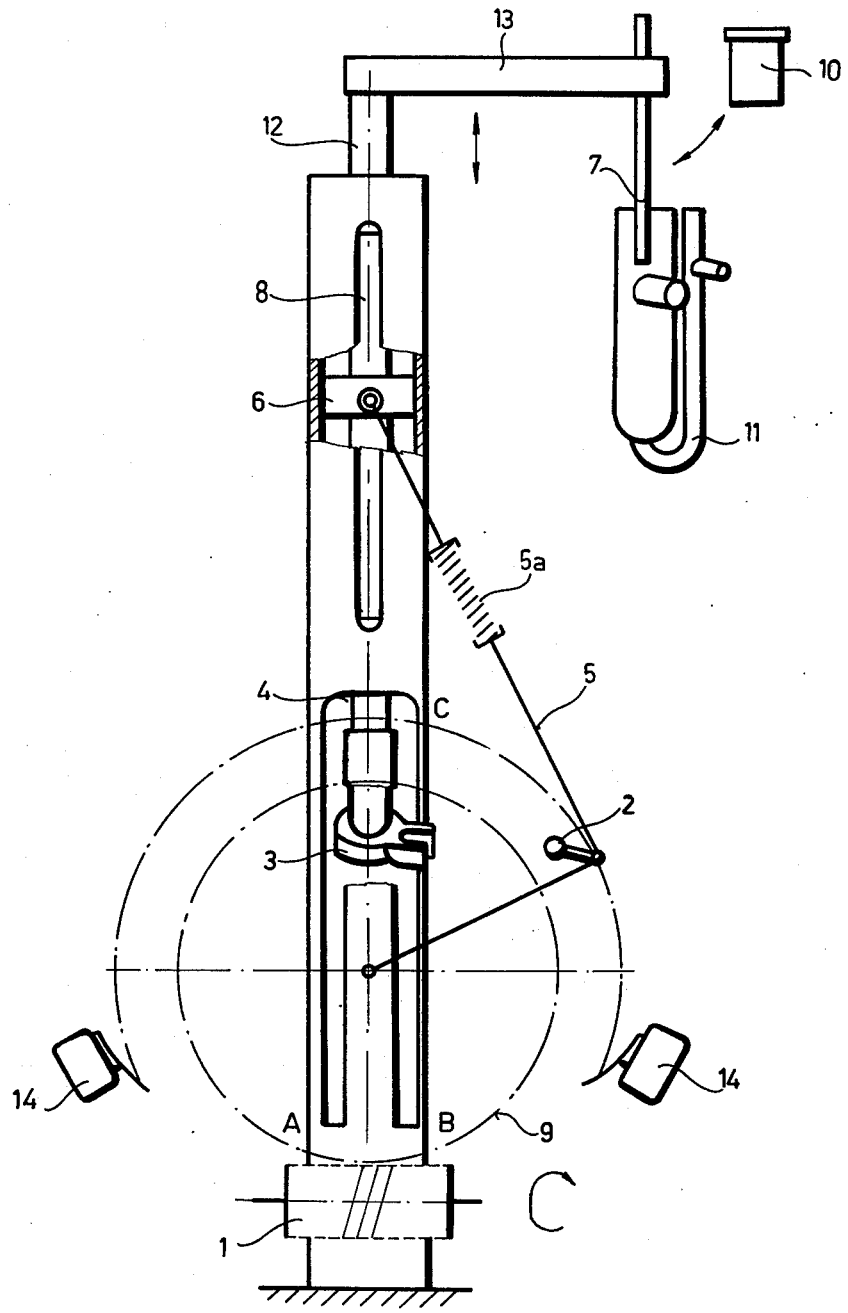

RAPID-ACTION AUTOMATIC SAMPLING APPARATUS

This invention concerns rapid-action automatic sampling apparatus, comprising an intermittently operated sampling probe immersible alternately into sampling vessels and washing vessels.

In known sampling apparatus the displacement of the sample-removing heads (heads for lifting out samples) has been achieved by means of complicated mechanisms including cams, levers and springs. A disadvantage of known mechanisms, i.e. sampling heads, is that their operation is slow, owing to the complexity of the construction. As a consequence of the use of a large number of constructional components, the wear that inevitably occurs results in inaccurate adjustment and thus their operation becomes critical. With these mechanisms the drawback also exists that in given cases involving sample storage vessels containing upper and lower liquid phases they cannot provide the necessary lifting height, or can only do so by means of additional constructional elements, further complicating an already quite complex construction.

The development of automatic analysers enabled the speed of analysis tasks to be increased, which necessitates an increase in the speed of sampling also. This, of course, requires the speed of movement of the sampling head to be increased.

The known constructions comprising cams or forced connections, rollers and bellcrank levers cannot ensure sufficiently fast sampling probe displacement for rapid sample feeding, because of the inertia of the constructional elements.

Further, the volume of the samples required for analysis may be reduced by using sample storage vessels with conical bottoms. In this case, however, in the interest of reliably sucking out the small amount of sample, it has to be ensured that the sampling probe is set to the centre line of the sample-containing vessel and that the probe approaches the bottom of the sample-containing vessel to the same depth in every case.

In known constructions this can be achieved only at very great expense, due to the precision fitting of the numerous components. Moreover, wear arising in regular use makes it impossible to maintain the demanded accuracy for extended periods.

It has been attempted to solve the problem of guiding the sampling probe centrally by means of a parallelogram linkage. However, the above-mentioned problems arising from fitting and wear exist with this mechanism also.

The synchronisation of the transfer of the sample-containing vessels, the lifting out and further displacement of the sampling probe takes place in known apparatus by means of geared or Geneva mechanisms or of other mechanical control. In the known apparatus optimal co-ordination of the two different movements is not ensured. A further defect is that, partly because of noise and partly because of the rapid deterioration in service life, fast-operation cannot be achieved.

An aim of the invention is to eliminate, or to reduce, the above-listed drawbacks of known automatic sampling devices and to provide an automatic sampling device which enables the sampling probe to be moved into a washing vessel and from there to a sample-containing vessel within the short time necessary for rapid sample changing.

A task underlying the invention is to develop an automatic sampling device which has low inertia to make it possible to perform movements of short duration necessary for rapid serial tests as well as to enable these movements to be stopped quickly; and which solves, reliably and with the required accuracy, the problem of lateral and vertical positioning of the sampling probe, while ensuring long service life and obviating the need for fine-precision fittings and expensive mechanisms.

The invention is based on the discovery that the above requirements may be met by providing an automatic sampling apparatus wherein the sequential lifting, angular displacement and lowering of the element for moving the sampling probe is effected by one and the same pivoted crank mechanism of minimal inertia, and wherein there is no need for additional elements for positioning.

Accordingly, the invention consists in a rapid-action automatic sampling apparatus comprising an intermittently operable sampling probe which is immersible alternately into sample-containing vessels and a washing vessel. The essence of the invention is that the sampling probe is arranged on a probe-carrying arm secured to the end of a vertical lifting rod which is journalled for axial displacement and for rotation about its own axis and which is connected with a crank mechanism for lifting or lowering the said rod, and that a mechanism for rotating the lifting rod between two positions is arranged on the lifting rod, the mounting of the lifting rod and the swivel arm of the crank mechanism.

To eliminate the danger of stressing the mechanism for moving the sampling probe, the swivel arm of the crank mechanism is preferably formed with a spring element so that its arm length may be varied resiliently.

The invention is described in detail, by way of example only, with reference to the accompanying purely diagrammatic kinematic drawing, which is a part-sectional, part-elevational view of the sampling apparatus according to the invention.

Referring to the drawing, the reference numbers 10 and 11 respectively designate a sample-containing vessel and a washing vessel. A sampling probe 7, which is alternately to be dipped into the sample-containing vessel 10 and the washing vessel 11, is secured to one end of a probe carrier arm 13. The end of the probe carrier arm 13 remote from the sampling probe 7 is secured at right angles to the end of a lifting arm 12. The lifting arm 12 is mounted for rotation about its own axis and for movement along its axis, as is indicated by arrows. A lifting hub 6 is arranged on the lifting rod 12. The connection between the lifting hub 6 and the lifting rod 12 is such that the lifting rod moves with the hub 6 vertically, but at the same time it can rotate relative to the hub 6.

The probe receives the drive for its displacement from a non-illustrated motor by way of a worm 1 and worm wheel 9. The worm wheel 9 is pivotally connected with one end of a swivel arm 5 with which it forms a crank mechanism. The other end of the swivel arm is articulated to the hub 6. A spring 5a is inserted into the swivel arm so that its length may resiliently vary.

A turning fork 3 is fixed on the lifting rod 12, while a turning pin 2 is fixed to the crank mechanism, the arrangement being such that in an appropriate position the pin 2 and the fork 3 can mesh or engage each other.

To guide the turning fork 3, an inverted U-shaped groove 4 is formed on the journal or mounting of the lifting rod 12. Two limit switches 14 defining end positions are located in the path of movement of the crank mechanism.

To ensure that the sampling probe is immersed to the same depth every time in the sample-containing vessel, the hub 6 moving vertically with the lifting rod 12 is provided with a lug that moves in a recess or groove 8 formed in the mounting or frame of the lifting rod 12. The lower end of the recess or groove 8 accurately determines the lowermost position of the sampling probe 7. The spring 5a of the swivel arm 5 is provided to eliminate or reduce stresses arising from the rigid abutment.

The mechanism illustrated in the drawing operates as follows. When the non-illustrated motor is started up, the worm 1 is rotated to rotate the worm wheel 9, let it be assumed initially in a counterclockwise direction, and the worm wheel 9 lifts, via the swivel arm 5, the hub 6 and thus the lifting rod 12.

Near the uppermost position of the lifting rod 12 and the pin 2 of the crank mechanism engages in the fork 3 fixed on the lifting rod. As the pin 2 rotates further, the fork 3 is rotated to its other position. Thereafter the crank mechanism will move downwardly, pulling the hub 6 and the lifting rod 12 down. The fork 3 moves downwardly in limb A of the inverted U-shaped guiding groove 4. When the lowermost position of the lifting rod 12, and thus of the sampling probe 7, has been reached, the crank mechanism actuates the left-hand limit switch 14 to stop the entire movement.

By changing the direction of rotation of the non-illustrated motor the movement can be reversed and started at the appropriate time.

As can be seen from the above-described preferred embodiment, the operation and construction of the mechanism are very simple. It enables the realization of very rapid and reliable feeding of sampled and washing liquid. In spite of the large accelerations the movement of the mechanism is substantially stress-free, and each time the sampling probe sets accurately to the lower centre point of the sample-containing vessels. The synchronisation of the displacement of the sampling probe and the sample-containing vessels is achieved by non-mechanical means and thus the velocity of both displacements may be optimised.

In an alternative, the pin 2 may be fixed on the lifting rod 12, the end of the swivel arm 5 being then pivotally connected to the pin 2; the groove 4 then guides the pin.

We claim as our invention:

1. Rapid-action automatic sampling apparatus comprising an intermittently operable sampling probe adapted for immersion alternately into a sample-containing vessel and a washing vessel, an arm for carrying the sampling probe, a vertically reciprocable lifting rod to which said arm is secured and which is, additionally, rotatable about its own longitudinal axis, a crank mechanism connected to said rod for lifting and lowering the latter, a swivel arm included in said crank mechanism, and a spring element included in the said swivel arm so that its arm length is resiliently variable, an angular displacement mechanism for rotating the said rod between two angular positions corresponding to the positions of said vessels, a mounting for the said rod enabling it to perform its reciprocatory and rotary movements, the said angular displacement mechanism being connected to the said rod, to the said mounting of the rod and to the said swivel arm, and driving means connectable to the said crank mechanism for driving the latter.

2. Rapid-action automatic sampling apparatus comprising an intermittently operable sampling probe adapted for immersion alternately into a sample-containing vessel and a washing vessel, an arm for carrying the sampling probe, a vertically reciprocable lifting rod to which said arm is secured and which is, additionally, rotatable about its own longitudinal axis, a crank mechanism connected to said rod for lifting and lowering the latter, a swivel arm included in said crank mechanism, an angular displacement mechanism for rotating the said rod between two angular positions corresponding to the positions of said vessels, a mounting for the said rod enabling it to perform its reciprocatory and rotary movements, the said angular displacement mechanism being connected to the said rod, to the said mounting of the rod and to the said swivel arm, and driving means connectable to the said crank mechanism for driving the latter, two limit switches being provided for limiting the rotation of the crank mechanism and for providing a signal to reverse the direction of the drive of the driving means, whereby in use the crank mechanism reciprocatingly between the said two positions.

* * * * *